United States Patent [19]

Goi et al.

[11] Patent Number: 4,841,144
[45] Date of Patent: Jun. 20, 1989

[54] DUST-PROOF TUBE HAVING A CYLINDRICAL PORTION THAT SEALS PHOTOSENSOR AND INTEGRALLY FORMED FRUSTRUM PORTION

[75] Inventors: Kouichi Goi, Kawasaki; Hiroshi Emori, Koshigaya; Daiki Sato, Tokyo, all of Japan

[73] Assignee: Laurel Bank Machines Co., Ltd., Tokyo, Japan

[21] Appl. No.: 160,769

[22] Filed: Feb. 26, 1988

[30] Foreign Application Priority Data

Feb. 27, 1987 [JP] Japan .............................. 62-29813[U]

[51] Int. Cl.⁴ .................................................. H01J 5/02
[52] U.S. Cl. .................................................... 250/239
[58] Field of Search .................... 250/223 R, 239, 571; 313/239, 242

[56] References Cited

U.S. PATENT DOCUMENTS

| | | | |
|---|---|---|---|
| 2,675,488 | 4/1954 | Bickley | 250/223 R |
| 2,688,099 | 8/1954 | Bickley | 250/239 |
| 3,235,739 | 2/1966 | Rottman | 250/223 R |
| 3,433,967 | 3/1969 | Bernheim | 250/239 |
| 3,536,831 | 9/1968 | Kanemaki et al. | 250/239 |
| 3,557,376 | 1/1971 | Senyk | 250/239 |
| 3,922,557 | 11/1975 | Carnes, Jr. | 250/571 |
| 4,384,303 | 5/1983 | Brenke et al. | 250/223 R |

Primary Examiner—David C. Nelms
Assistant Examiner—William Oen
Attorney, Agent, or Firm—Fleit, Jacobson, Cohn, Price, Holman & Stern

[57] ABSTRACT

A dust-proof tube for a photosensor including of a cylindrical portion having a thick wall and substantially the same length as that of the photosensor, the inner diameter of the cylindrical portion being substantially equal to the outer diameter of the photosensor so that the cylindrical portion can receive the photosensor sealingly, and a frustum portion integrally formed with the cylindrical portion and extending from the end of the cylindrical portion, the cylindrical portion and the frustum portion being made of elastic material.

13 Claims, 2 Drawing Sheets

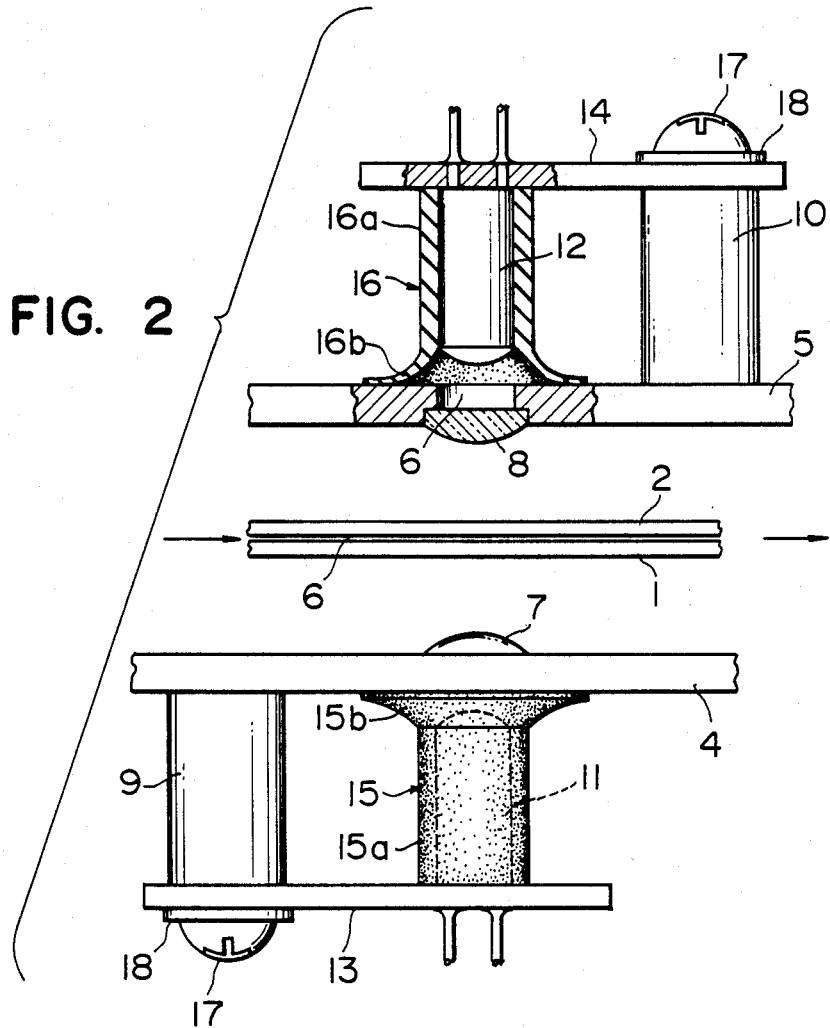

DUST-PROOF TUBE HAVING A CYLINDRICAL PORTION THAT SEALS PHOTOSENSOR AND INTEGRALLY FORMED FRUSTRUM PORTION

BACKGROUND OF THE INVENTION

The present invention relates to a dust-proof tube for a photosensor and, more particularly, to such a tube for a photoemitting element or a photoreceiving element.

DESCRIPTION OF PRIOR ART

Unexamined Japanese Utility Model Publication No. 57-116647 discloses a dust-proof tube for a photosensor which airtightly covers a photoemitting element or a photoreceiving element and which has a vertical transparent wall intersecting the axis of light emitted in the oblique direction from the photoemitting element. According to the prior art tube, since it is possible to prevent some dust from entering the tube airtightly covering the photoemitting element or the photoreceiving element and the wall of the tube intersecting the light axis is arranged vertically, it is possible to limit dust from attaching to the photosensor and the surface of the wall, thereby protecting to some extent the sensing accuracy of the photosensor.

However, since it is difficult to form the prior art tube to be sufficiently airtight, it is not possible to completely prevent dust from entering the tube and, therefore, from attaching to the surface of the vertical wall of the prior art tube. As a result, sensing errors are unavoidable.

Further, since it is not easy to position the wall of the tube intersecting the light axis precisely vertically, it is difficult to position the tube again after cleaning or repairing it.

SUMMARY OF THE INVENTION

It is therefore the object of the invention to provide a dust-proof tube for the photosensor which protects a photosensor from dust and which can be easily maintained.

According to the present invention, the above and other objects can be accomplished by a dust-proof tube for a photosensor comprising a cylindrical portion, the inner diameter of said cylidrical portion being substantially equal to the outer diameter of said photosensor so that said cylindrical portion can receive said photosensor sealingly, and a frustum portion integrally formed with said cylindrical portion and extending from the end of said cylindrical portion, said cylindrical portion and said frustum portion being made of elastic material.

The above and other objects and features of the present invention will become apparent from the following description taken in conjunction with reference to the accompanying drawings.

BRIEF DESCRIPTION OF THE DRAWINGS

FIG. 2 is a schematic drawing showing a side view of the sensor unit including dust-proof tubes for photosensors which are embodiments of the present invention.

DESCRIPTION OF THE PREFERRED EMBODIMENTS

Figure 1:
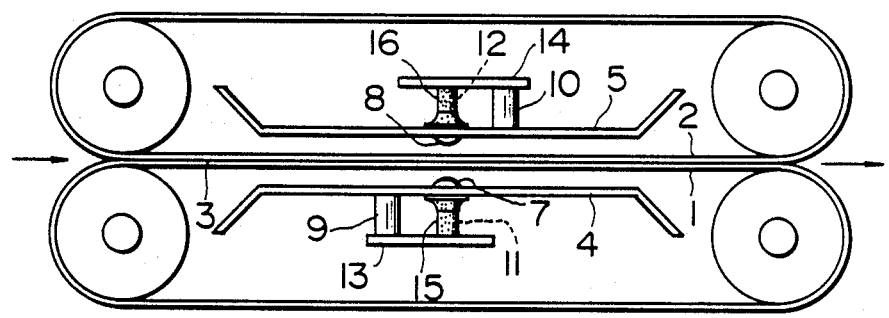
FIG. 1 is a schematic drawing showing a partial side view of a sheet transporting apparatus including a dust-proof tube for a photosensor which is an embodiment of the present invention.
Figure 3:
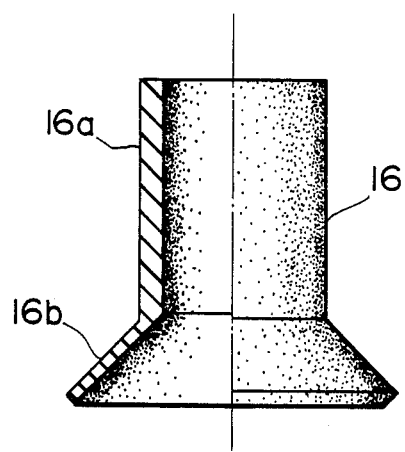
FIG. 3 is a schematic drawing showing a partial cross-sectional view of a dust-proof tube for photosensors which is an embodiment of the present invention.

Referring to FIG. 1, there is shown a part of a sheet transporting apparatus in which there is provided a pair of endless transporting belts 1 and 2 for transporting sheets in the direction as indicated by arrows by holding them between the surfaces thereof. On both outer sides of a transporting path 3 where the transporting belts 1 and 2 contact with each other, that is, on the respective inner sides of the endless transporting belts 1 and 2, sensor supports 4 and 5 for supporting a sensor thereon are arranged parallel to the transporting path 3. As can be seen in the detailed structure shown in FIG. 2, each of the sensor supports 4 and 5 is formed with a small hole 6, the respective holes 6 being arranged symmetrically with respect to the transporting path 3 and each being provided with cover lenses 7, 8 on the side of the transporting path 3. Each of the sensor supports 4, 5 is integrally formed with collars 9, 10 on the surface opposite to the cover lenses 7, 8. Within each of the collars 9, 10, there is formed an internal thread (not shown). Photosensors 11, 12, one of which is a photoemitting element and the other of which is a photoreceiving element, are respectively secured to sensor boards 13, 14 and inserted into sensor tubes 15, 16. Each of the sensor tubes 15, 16 is made of elastic material and, as shown in FIG. 3, consists of a cylindrical portion 15a, 16a having a thick wall and the same length as that of each photosensor 11, 12, the inner diameter of which is substantially the same as the outer diameter of each photosensor 11, 12 so that the sensor tube 15, 16 can receive the photosensor 11, 12 sealingly, and a frustum portion 15b, 16b having a thin wall, the frustum portion 15b, 16b being formed integrally with the cylindrical portion 15a, 16a and extending from the end of the cylindrical portion 15a, 16a. The overall length of each sensor tube 15, 16 is longer than that of each collar 9, 10.

When mounting the photosensors 11, 12 in the sheet transporting apparatus, each of the photosensor 11, 12 is inserted into a sensor tube 15, 16 until the end of the sensor tube 15, 16 makes contact with the sensor board 13, 14 and the photosensor 11, 12 is received sealingly by the sensor tube 15, 16. Then, the sensor tube 15, 16 which has received the photosensor 11, 12 attached to the sensor board 13, 14 is set on the sensor support 4, 5 such that the end of the frustum portion 15b, 16b thereof is in contact with the surface of the sensor support 4, 5 around the hole 6 and the cover lens 7, 8. And each of the collars 9, 10 is secured to the sensor board 13, 14 by a screw 17 and a washer 18. Since the overall length of the sensor tube 15, 16 is longer than that of the collar 9, 10 and the frustum portion 15b, 16b of the sensor tube is formed by the thin wall made of elastic material, the frustum portion 15b, 16b is deformed so that the open end portion thereof is enlarged. Thus, the sensor tubes 15 and 16 receiving the photosensors 11, 12 are airtightly secured to the sensor supports 4, 5.

When securing the sensor tubes 15, 16 to the sensor supports 4, 5, it is preferable to press the sensor tube 15, 16 so that the overall length thereof becomes shorter than the length of the collar 9, 10, that is, the distance between the sensor support 4, 5 and the sensor board 13, 14, and then the collars 9, 10 is secured to the sensor board 13, 14 by the screw 17 and the washer 18. More specifically, when the sensor tube 15, 16 is pressed on the sensor support 4, 5 in this way, the part of the air within the sensor tube 15, 16 is forced out between the bottom of the frustum portion 15b, 16b and the surface of the sensor support 4, 5. Moreover, a force of restoration arises within the elastic material forming the sensor tube 15, 16 and this force acts to increase the height or the inner volume of the sensor tube 15, 16. Any increase in the height or the inner volume of the sensor tube 15, 16 tends to reduce the pressure of the air therein since no air can be drawn in between the bottom of the frustum portion 15b, 16b and the surface of the sensor support 4, 5. As a result, when the height of the sensor tube 15, 16 becomes equal to the distance between the sensor support 4, 5 and the sensor board 13, 14, the height of the sensor tube 15, 16 does not increase any more and the sensor tube 15, 16 can be secured to the sensor supports 4, 5 airtightly by virtue of the negative pressure therein and the pressure force acting thereon from the sensor support 4, 5 and the sensor board 13, 14. Thus securement of the sensor units 19 comprising the photosensor 11, 12 and the sensor tube 15, 16 to the sheet transporting apparatus is finished.

As described above, the photosensors 11, 12 are secured on the respective sensor supports 4, 5 so as to face each other and such that the cover lenses 7, 8 are close to the transporting path 3. The sensor units 19 are thus screened from light when the sheet transporting operation is started.

According to the above-described embodiment, since the sensor tubes 15, 16 receiving the photosensor 11, 12 therein are substantially completely sealed up, it is possible to protect the photosensors 11, 12 from dust and sensing errors can be minimized. Further, since the sensor tubes 15, 16 are pressed onto the sensor supports 4, 5 so that the frustum portions 15b, 16b are deformed, in the case where external force such as vibration acts on the photosensor unit 19, the frustum portions 15b, 16b stick in pressure contact with the surface of the sensor supports 4, 5 to prevent dust from entering into the sensor tubes 15, 16. Furthermore, since the cover lenses 7, 8 are disposed close to the transporting path 3, even if dust attaches to the surface of the cover lenses 7, 8, it is removed by air accompanying the transporting belts 1, 2 and/or the belts 1, 2 themselves and the sensing accuracy is not lowered by dust attached to the cover lenses 7, 8. Moreover, since the photosensors 11, 12 and the sensor tube 15, 16 can be removed from the sheet transporting apparatus by releasing the screw 17, it is very easy to clean and repair the photosensors 11, 12.

As described above with respect to the preferred embodiment, according to the present invention, it is possible to obtain a dust-proof tube for a photosensor capable of sufficiently preventing dust from attaching to the photosensor and improving the sensing accuracy of the photosensor.

The present invention has thus been shown and described with reference to the specific embodiment. However, it should be noted that the present invention is in no way limited to the details of the described arrangements but changes and modifications may be made without departing from the scope of the appended claims.

For example, although the wall of the frustum portion 15b, 16b of the sensor tube 15, 16 is formed thinner than that of the cylindrical portion 15a, 16a in the above-described embodiment, since the sensor tube 15, 16 is made of elastic material and can be deformed by pressure, it may not be necessary for the wall of the frustum portion 15a, 16a to be thinner than that of the cylindrical portion 15a, 16a.

Further, in the above-described embodiment, although the length of the sensor tube 15, 16 is substantially the same as that of the photosensor, 11, 12, it may be sufficient for the length of the photosensor 11, 12 to be shorter than the overall length of the sensor tube 15, 16 when the sensor tube 15, 16 is pressed by the sensor support 4, 5 and the sensor board 13, 14.

We claim:

1. A dust-proof tube for a photosensor comprising a cylindrical portion, the inner diameter of said cylindrical portion being substantially equal to the outer diameter of said photosensor so that said cylindrical portion can sealingly receive said photosensor, and a frustum portion integrally formed with said cylindrical portion and extending from an end of said cylindrical portion, said cylindrical portion and said frustum portion being made of elastic material.

2. A dust-proof tube for a photosensor in accordance with claim 1 in which said photosensor is a photoemitting element or a photoreceiving element.

3. A dust-proof tube for a photosensor in accordance with claim 2 in which said cylindrical portion has substantially the same length as that of said photosensor.

4. A dust-proof tube for a photosensor in accordance with claim 2 in which said cylindrical portion has a thick wall and said frustum portion has a thin wall.

5. A photosensor unit for a sheet transporting apparatus having two belt means for transporting sheets by holding said sheets therebetween, said photosensor unit comprising photosensor means, sensor tube means for said photosensor means, said sensor tube means being made of elastic material and including a cylindrical portion and a frustum portion which are formed integrally, sensor supporting means for supporting said sensor tube means thereon, said sensor supporting means having a hole transmitting light, said hole having a transparent cover lens facing one of said belt means and disposed close to said belt means, and sensor board means for carrying said photosensor means, said sensor tube means receiving said photosensor means and being secured to said sensor supporting means and said sensor board means by being pressed thereby.

6. A photosensor unit in accordance with claim 5 in which said photosensor means is a photoemitting element or a photoreceiving element.

7. A photosensor unit in accordance with claim 5 in which the inner diameter of said cylindrical portion is substantially equal to the outer diameter of said photosensor.

8. A photosensor unit in accordance with claim 6 in which the overall length of said sensor tube means is longer than the distance between said sensor supporting means and said sensor board means.

9. A photosensing device for a sheet transporting apparatus including two belt means for transporting sheets by holding said sheets therebetween, said photosensing device comprising a photoemitting element, a photoreceiving element, first sensor tube means for said photoemitting element, second sensor tube means for said photoreceiving element, said first and second sensor tube means being made of elastic material and including a cylindrical portion and a frustum portion which are formed integrally, first sensor supporting means for supporting said first sensor tube means thereon, second sensor supporting means for supporting said first sensor tube means thereon, said first and second sensor supporting means having a hole transmitting light, said hole having a transparent cover lens facing one of said belt means and disposed close to said belt means, first sensor board means for carrying said photoemitting element, and second sensor board means for carrying said photoreceiving element, said first sensor tube means receiving said photoemitting element and being secured to said first sensor supporting means and said first sensor board means by being pressed thereby, said second sensor tube means receiving said photoreceiving element and being secured to said second sensor supporting means and said second sensor board means by being pressed thereby.

10. A photosensor arrangement comprising photosensor means, dust-proof tube means for receiving said photosensor means therein, said dust-proof tube means including a cylindrical portion, the inner diameter of said cylindrical portion being substantially equal to the outer diameter of said photosensor means so that said cylindrical means can sealingly receive said photosensor means, and a frustum portion integrally formed with said cylindrical portion and extending from the end of said cylindrical portion, said cylindrical portion and said frustum being made of elastic material.

11. A photosensor arrangement in accordance with claim 10, in which said photosensor means is a photoemitting element or a photoreceiving element.

12. A photosensor arrangement in accordance with claim 11, in which said cylindrical portion has substantially the same length as that of said photosensor means.

13. A photosensor arrangement in accordance with claim 11, in which said cylindrical portion has a thick wall and said frustum portion has a thin wall.

* * * * *